United States Patent [19]
Fisher

[11] Patent Number: 5,197,481
[45] Date of Patent: Mar. 30, 1993

[54] NON-INVASIVE METHOD AND APPARATUS FOR MEASURING MIXED VENOUS BLOOD PRESSURE (PVCO2) AND OTHER PHYSIOLOGICAL VARIABLES

[76] Inventor: Joseph Fisher, 113 Franmore Cir., Thornhill, Ontario, Canada L4J 3B9

[21] Appl. No.: 417,070

[22] Filed: Oct. 4, 1989

Related U.S. Application Data

[62] Division of Ser. No. 912,969, Sep. 29, 1986, Pat. No. 4,947,860.

[30] Foreign Application Priority Data

Oct. 10, 1985 [CA] Canada .................................. 492766

[51] Int. Cl.$^5$ .............................................. A61B 5/08
[52] U.S. Cl. ................................................. 128/719
[58] Field of Search ............................. 128/718, 719

[56] References Cited

U.S. PATENT DOCUMENTS 3,507,146  4/1970  Webb ................................. 128/719
4,221,224  9/1980  Clark ................................. 128/718
4,608,995  9/1986  Linnarsson et al. ............ 128/719

FOREIGN PATENT DOCUMENTS 2912391 10/1980 Fed. Rep. of Germany ...... 128/719

OTHER PUBLICATIONS

Suzuki et al., "The Development . . . Analyzer", The Trans IECE Japan, vol. E63, No. 11, 1980, pp. 819–820.
NASA Tech Briefs, "Constraint Free Measurement", Spring 1981, p. 46–47.
Wessel et al., "Minicomputer . . . Gas Exchange", Computers in Cardiology, 1978, pp. 97–104.
Gedeon et al., "A New Method . . . flow", Med & Biol. Eng. & Comput., 1980, 18, pp. 411–418.

*Primary Examiner*—Lee S. Cohen
*Attorney, Agent, or Firm*—Ivor M. Hughes

[57] ABSTRACT

A method of determining the mixed venous PCO$_2$ (PvCO$_2$) is disclosed, the method comprising the steps of:
(a) measuring the PCO$_2$ of the gases inhaled and exhaled by the patient under controlled conditions without rebreathing;
(b) causing the patient to inhale a test gas containing at least a small concentration of CO$_2$ and continuing to measure the PCO$_2$ of the inspired and expired gases, the patient taking at least two breaths without rebreathing;
(c) determining the PCO$_2$ of the inspired gases (P$_I$CO$_2$) and the end tidal PCO$_2$ of expired gased (PECO$_2$);
(d) determining the differences between the end tidal PCO$_2$ and inspired PCO$_2$ under control and test conditions, and relating it to the inspired PCO$_2$ used in the determination of the difference. This relationship can be used to calculate the mixed venous PCO$_2$.

25 Claims, 5 Drawing Sheets

FE-FI VS FI FOR N2

NON-INVASIVE METHOD AND APPARATUS FOR MEASURING MIXED VENOUS BLOOD PRESSURE (PVCO₂) AND OTHER PHYSIOLOGICAL VARIABLES

This is a division of application Ser. No. 06/912,969, filed Sep. 29, 1986, now U.S. Pat. No. 4,947,860.

FIELD OF INVENTION

This invention relates to a method and apparatus for automatically and non-invasively measuring the partial pressure of carbon dioxide in the mixed venous blood ($PvCo_2$) and a number of other physiological variables that relate to the function of the cardio-respiratory system.

BACKGROUND OF THE INVENTION

Intensive medical management of critically ill patients or patients undergoing operations which result in severe physiological disturbances requires detailed monitoring of the cardio-respiratory system. At present the apparatus used to provide such monitoring frequently require insertion into the body. For example, a pulmonary artery catheter must be inserted through the skin, into a major vessel and passed along the vessel, through the heart chambers into the pulmonary artery. The use of such monitoring devices add their own morbidity and mortality to the patient's underlying illness. These risks must always be weighed against the possible benefit of the information gained.

A non-invasive monitor would be of great benefit in that it would decrease the discomfort and risk of added morbidity and mortality to patients already very ill. It would further have application where such test information is required but invasive techniques are unjustified (in ambulatory patients and athletes) or impossible to institute (small infants).

In the prior art there are several non-invasive methods of obtaining $PvCO_2$. These methods are based on the principle of using the lungs as a chamber that comes into equilibrium with the partial pressure of a gas dissolved in a liquid, that is, an aerotonometer, whereby the lung gases are brought into equilibrium with the gases dissolved in the inflowing pulmonary artery blood. This equilibrium must be reached before recirculated blood with altered gas concentrations reaches the lungs.

ONE METHOD: EQUILIBRIUM BY BREATH-HOLDING

This technique is reviewed in detail by Grollman (Grollman, A., *The Cardiac Output of Man in Health and Disease*. Charles C. Thomas 1932, p. 25-26). When a subject holds his breath, the partial pressure of carbon dioxide in the alveolar air ($PACO_2$) gradually increases at a decreasing rate of increase as it approaches the $PvCO_2$. Equilibration is recognized by a constant $PCO_2$ in several succesive samples.

When room air is inhaled, the amount of $CO_2$ that diffuses into the lungs is insufficient to equilibrate the $PACO_2$ with the $PvCO_2$ within a recirculation time of about twenty seconds. Grollman (Grollman, A., *The Cardiac Output of Man in Health and Disease*. Charles C. Thomas 1931 p. 28) describes a method where before breath-holding the subject inspires a gas containing a concentration of $CO_2$ determined by trial and error to give a constant $PCO_2$ on successive expiratory samples. Dubois et al. (Dubois, A.B., Britt, A.G., Fenn, W.O.; *Alveolar CO₂ During the Respiratory Cycle*. Jour. App. Physical 4:535 1952) have demonstrated that the rise of $CO_2$ during breath-holding can be accurately approximated by a single exponential. Frankel et al. (Frankel, D.Z.N., Sandham, G., Rebuck, A.S.; *A Noninvasive Method for Measuring the $PCO_2$ of Mixed Venous Blood*. American Rev. Resp. 0.5 117:63, 1978) describe a technique where the patient breath-holds either 100% $O_2$ or 12% $CO_2$ in $O_2$. The subject's breath was held in inspiration by an occlusive solenoid valve controlled manually by the investigators. At the end of five seconds and ten seconds, a 500 ml sample of expired gas was collected and analyzed. Using a formula similar to Dubois, the $PvCO_2$ was calculated by extrapolating the points to an asymptote which is claimed to represent the $PvCO_2$. Frankel, Sandham and Rebuck (Frankel, D.Z.N., Sandham G., Rebuck A.S.; *A New Method for Measuring $PCO_2$ During Anesthesia*, Br. v. Anaesth, 51, 215, 1979) used a similar technique on unconscious patients during anesthesia.

These breath-holding techniques have a number of serious drawbacks.

1) They require patient co-operation.
2) They are difficult for the patient to perform. Sick patients with respiratory disease are usually unable to take a breath consisting of 2 litres or more as required by the technique. They are seldom able to hold their breath in deep inspiration as required. This is especially true of Frankel's technique where inhalation of 12% $CO_2$ is required.
3) Even if the manoeuver is performed, it alters the very parameters one is trying to measure: The cardiac output, $PvCO_2$, and even the systemic arterial $PO_2$ ($PaO_2$).
4) Performance of the manoeuver may harm the patient by dropping his cardiac output, causing hypoxia and hypercarbia.
5) The data obtained is difficult to analyze. Fitting exponential curves to two points and extrapolating to an asymptote introduces mathematical difficulties and uncertainties to the measured variable. The cumbersomeness of the described methods illustrates why they cannot be used routinely in the clinical setting and why full automation has not been achieved.

ANOTHER METHOD OF NON-INVASIVELY OBTAINING PvCO₂: EQUILIBRATION BY REBREATHING

Rebreathing is conceptually very similar to breath-holding. In breath-holding, the lungs act as space in which the $PCO_2$ rises as a decreasing exponential towards the $PvCO_2$. With rebreathing, the closed space is expanded to include a container attached to the lungs in which the gases are mixed by passing the gas back and forth between the container and the lung. Even to a greater extent than with the breath-holding, the amount of $CO_2$ entering the closed system is insufficient to effect an equilibrium with the mixed venous $PCO_2$ within a blood recirculation time.

The rise in $PCO_2$ in the closed system with time is also exponential. Defares (Defares, J.G. *Determination of PVCO₂ From the Exponential $CO_2$ Rise Rebreathing*, Appl. Physiol. 13 (2): 159-164, 1958) used repeated or constant sampling of $PCO_2$ as gas is rebreathed from the container to extrapolate to a final equilibrium $PvCO_2$ value.

Others have employed various techniques to add an amount of $CO_2$ to the rebreathing container that would result in a constant $PCO_2$ in the closed system, indicating equilibration with $PvCO_2$. These are reviewed in more detail by Grollman (Grollman, A. *The Cardiac Output of Man in Health and Disease*. Charles C. Thomas, 1932 pg. 17-25) and Richards and Strauss (Richards, D.W. Jr., Strauss, M.L., *Carbon Dioxide and Oxygen Tensions of the Mixed Venous Blood of Man at Rest*. J. Clin Investig, 9:475, 1930). Douglas and Haldane (Douglas C.G., Haldane J.S.; *The Regulation of the General Circulation Rate in Man*. J. Physiol 56:69, 1922) filled a bag with 6.5%-10% $CO_2$, rebreathed its contents twice, then performed a breath-holding manoeuver. In 1922 Meakins and Davies rebreathed into a container for about twenty seconds, rested and again rebreathed into the same container. This intermittent rebreathing was repeated until the $PCO_2$ in the container was constant. More recently Collier (Collier, C.R., *Determination of Mixed Venous $CO_2$ Tensions by Rebreathing*. J. App Physiol 9:25, 1956.) described a technique using rebreathing and monitoring of inspired and expired $PCO_2$ using a device for continuous measuring $CO_2$ (or a capnograph). By trial and error, the appropriate initial partial pressure of $CO_2$ (or $PCO_2$) of the rebreathing container is found for a particular patient. He then rebreathes from this container. Before one blood recirculation time, an equilibrium may be established with the $PvCO_2$ as indicated by a plateau of the capnograph tracing. Powles and Campbell (Powles A.C.P., Campbell, E.J.M.; *An Improved Rebreathing Method for Measuring Mixed Venous $CO_2$ Tension and its Clinical Application*. Can. Med. Ass. Jour. 118:501, 1978) outlined this application of the technique to the clinical setting and characterized further the appropriate capnograph equilibrium plateau. Franciosa (Franciosa, J.A.; *Evaluations of the $CO_2$ Rebreathing Cardiac Output Method in Seriously Ill Patients*. Circulation 55(3): 449, 1977) also describes the clinical application of the rebreathing technique.

Rebreathing techniques have a number of serious shortcomings.

1) They are very cumbersome requiring a large amount of manipulation of equipment. The rebreathing container must be filled to a critical size and $CO_2$ partial pressure, which may be different for each patient. Powles (Powles, A.C.P., Campbell, E.J.M.; *An Improved Rebreathing Method for Measuring Mixed Venous $CO_2$ Tension and Its Clinical Application*. Can. Med. Ass. Jour. 118:508, 1978.) and Franciosa (Franciosa J.A.; *Evaluation of the $CO_2$ Rebreathing Cardiac Output Method in Seriously Ill Patients*. Circulation 5:5(3): 449, 1977) say they go through the test five to six times before the appropriate combination can be found.

2) The patient is required to perform manoeuvers. Franciosa's patients must take deep breaths and breathe to a metronome.

3) Data is difficult to interpret. Powles, in discussing his end point plateau, illustrates three separate plateaus. To pick the appropriate one requires considerable expertise and may in fact be impossible. Its use on ventilated patients has not yet been described. These drawbacks preclude widespread routine clinical use or automation. *Another Method of Non-Invasively Obtaining $PvCO_2$*, Prolonged Exhalation Kim et al (Kim, T.S., Rahn, H., Farhi, L.E.; *Estimation of True Venous and Arterial $PCO_2$ by Gas Analysis of a Single Breath*. J. Appl. Physiol 21(4):1338, 1966) describe a method for arriving at the $PvCO_2$ from a single breath. The subject must take a deep breath of ambient atmosphere and exhale over ten or more seconds. Kim et al continuously monitor $PO_2$ and $PCO_2$. They use the relative values of $PO_2$ and $PCO_2$ to predict $PvCO_2$.

This technique again has the drawback that it requires a critical patient manoeuver. It has not been used in ventilated or ill patients. Its theory and application is difficult. It therefore does not lend itself to automation or manual application in the clinical situation.

As stated by Grollman (Grollman A., *The Cardiac Output of Man in Health and Disease*. Charles C. Thomas, 1932, pg. 17-25), the techniques for determination of $PvCO_2$ "consist, for the most part, of various rebreathing procedures or procedures involving more complex respiratory gymnastics" such as breath-holding and prolonged exhalations.

It is therefore an object of this invention to provide a method and apparatus whereby $PvCO_2$ can be obtained, non-invasively while the patient continues to breathe in his/her usual manner.

It is a further object of this invention to provide a method and apparatus where $PvCO_2$ can be obtained:

1) whereby the patient need not hold his breath, rebreathe or provide prolonged exhalations, 2) that is independent of the patient's tidal volume, respiratory frequency or pattern of ventilation, 3) that works equally well in intubated and mechanically ventilated patients as it does in those breathing spontaneously, 4) that does not require a change in the patient's inspired oxygen concentration, 5) from data that can be plotted on linear curves, 6) where the mathematics is therefore readily understandable and the end point is easily calculated, and 7) automatically with minimal manipulation of hardware and no operator-performed data analysis or calculations.

Further and other objects of the invention will be apparent to a man skilled in the art from the following summary of the invention and detailed description of the embodiments.

SUMMARY OF INVENTION

According to one aspect of the invention a method of determining the mixed venous $PCO_2$ ($PvCO_2$) is provided, the method comprising the steps of:

(a) measuring the $PC_2$ of the gases inhaled and exhaled by the patient under control conditions without rebreathing;

(b) causing the patient to inhale a test gas containing at least a small concentration of $CO_2$ and continuing to measure the $PC_2$ of the inspired and expired gases (the patient taking at least two breaths and preferably three or four breaths of the test gas without rebreathing);

(c) determining the $PC_2$ of the inspired gases ($PIC_2$) and the end tidal $PC_2$ of expired gases ($PEC_2$);

(d) determining the difference between the end tidal $PC_2$ and inspired $PC_2$ under control and test conditions (in the test conditions preferably after inhaling the third or fourth breath of a test gas), and relating it to the inspired $PC_2$ used in the determination of the difference.

(e) This relationship is linear. Any two points relating $PECO_2 - P_ICO_2$ to $P_ICO_2$, will define a straight line. This line can be determined mathematically including graphically by using at least two points generated as described in sub-paragraphs (a) to (d) inclusive. The $PIC_2$ calculated using this relation yields $PvCO_2$ when $PECO_2 - PIC_2 = 0$.

According to another aspect of the invention, there is provided an apparatus for determining the mixed venous $PC_2$ ($PvCO_2$) comprising:

(a) means for measuring the $PC_2$ of the gases inhaled and exhaled by the patient under control conditions without rebreathing, (b) means for permitting the patient to inhale a test gas containing at least a small concentration of $C_2$ without rebreathing and means for measuring the $PC_2$ of the inspired and expired gases that result from breathing the test gases (preferably including means for controlling the number of breaths of test gas taken, for example three or four), (c) a reservoir for the inhaled test gases containing at least a small concentration of $C_2$.

According to another aspect of the invention, the apparatus may further comprise means to determine the difference between the end tidal $PC_2$ and inspired $PC_2$ under control and test conditions and means for relating said difference to the inspired $PC_2$ used in the determination of said difference to mathematically determine the $PvCO_2$.

In one embodiment, the means for measuring the $PC_2$ of the gases inhaled and exhaled by the patient under control and test conditions comprises a capnograph (or mass spectrometer).

In another embodiment the means permitting the patient to inhale the test gas containing at least a small concentration of $CO_2$ without rebreathing comprises:

(i) a manifold having ports therein one port for communicating with the mouth of the patient, another port for permitting exhaled gases to escape to the atmosphere, another port for permitting entry of the test gas from the reservoir to the manifold and another port to permit entry of room air to the manifold for inhalation;

(ii) two one-way valves, one such valve positioned in the manifold between the exhalation port and the port leading to the reservoir to permit control gas and test gas to pass therethrough but preclude any exhaled gases from passing through it and the other such valves being positioned at the exhalation port permitting exhalation but precluding entry of room air during inhalation, (iii) a three-way valve in the manifold for alternately allowing control condition gas or test gas to pass through the port for communicating with the mouth of the patient.

In another embodiment (suitable for use with patients who are mechanically ventilated), the means permitting the patient to inhale the test gas containing the at least small concentration of $CO_2$ without rebreathing may comprise in addition to the manifold as constructed in the previous paragraph, another three-way valve which is positioned in the manifold on the side of the other three-way valve remote the port permitting exhalation of the expired gases, the three-way valve for alternately permitting gases to pass from a ventilator (where a ventilator is attached) to the port of the manifold through which ventilated gas may pass to the patient or be diverted to be used for pressurizing the reservoir containing the test gas to be delivered to the patient as for example in a secondary ventilator circuit. It is of course apparent to a man skilled in the art that the first three-way valve must be turned simultaneously with the other three-way valve in such a way as to permit the gases from either the ventilator or reservoir to pass through the part of the manifold leading to the patient's mouth.

In another embodiment, the means to determine the difference between the end tidal $PCO_2$ and inspired $PCO_2$ under control and test conditions and means for relating said difference to the inspired $PCO_2$ used in the determination of said difference may comprise machine intelligence means including a computer and requisite computer programs.

The method and apparatus may be employed for the calculation of other physiological parameters. For example by additionally measuring nitrogen or other insoluble gases using the same method substituting $N_2$ for $CO_2$ at a concentration other than the control concentration and taking the measurement on or after the first breath of $N_2$ or such other insoluable gas from the reservoirs, and knowing the tidal volume (which can be obtained by placing a measuring device for example pneumotachograph in for example the patient's mouth or in the manifold near the port through which the gases pass to the mouth), the functional residual capacity can be calculated. In addition, apparatus may be used similar to that described above including machine intelligence means which may be programmed to determine the difference between the $P_E N_2$ (or insoluble gas)-$P_I N_2$ (or insoluble gas) and related to the $P_I N_2$ (or insoluble gas) to determine the linear relationship therebetween and the slope of that relationship. Using the slope thus obtained and the tidal volume measured, the FRC (Functional Residual Capacity) is measured as follows:

$$FRC = \frac{V_T}{S+1} - V_T$$

where $V_T$ = Tidal Volume and $S$ = slope obtained from relationship $P_{EN2} - P_{IN2}$ versus $P_{IN2}$ which may be calculated graphically as well, without rebreathing.

If minute $CO_2$ production is also measured during the control phase (during other than test conditions), the mixed venous $PvCO_2$ as determined by the previously described method and/or apparatus, can be used to calculate cardiac output using a Fick Technique. If breath by breath, minute $CO_2$ production is calculated for different test gases, using my method and/or apparatus, the cardiac output can be easily derived as described by Gideon et al. *A New Method for Non-Invasive Determination of Pulmonary Blood Flow*, Med. and Biole Eng. Compute, Vol. 18, p. 411, 1980 which discloses the ventilating of a patient in steady state, the method of determining the cardiac output comprising the steps of:

(1) monitoring minute $CO_2$ production and end tidal $PCO_2$;

(2) introducing a change in minute $CO_2$ exhalation and observing the effect on end tidal $PCO_2$ by (a) providing an extra length of pause between breaths, keeping tidal volume and expiratory time constant; and (b) keeping tidal volume and expiratory time constant but adding $CO_2$ rebreathing to decrease effective alveolar ventilation to provide a change in the end tidal $CO_2$ concentration and (3) calculating output $\overset{\circ}{Q}$ by:

$$\overset{\circ}{Q} = \frac{1}{S} \times \frac{d\overset{\circ}{V}}{dPET}$$

where S is the slope of the CO₂ dissociation curve at a PCO₂ equal to the end tidal PCO₂; $d\dot{V}$ is the change in minute CO₂ exhaled during the step in paragraph 2 and dPET is the change in end tidal PCO₂ during the step in paragraph 2 and the steps of:

(a) measuring the PCO₂ of the gases inhaled ($PI_{co2}$) and exhaled by the patient under controlled conditions without rebreathing (b) causing the patient to inhale a test gas containing at lest a small concentration of CO₂ and continuing to measure the PCO₂ of the inspired and expired gases, the patient taking at least two breaths without rebreathing (c) determining the PCO₂ of the inspired gases ($P_1$) and the end tidal PCO₂ of expired gases (PECO₂)

(d) determining the differences between the end tidal PCO₂ and inspired PCO₂ under control and test conditions, relating these differences to the inspired PCO₂ to determine the mixed venous PCO₂ (PvCO₂) used to determine dPET wherein dPET is calculated utilizing the determination o the end tidal PCO₂ during control and test phases as referred to in subparagraphs (i) and (ii) as follows:

(i) measuring the PCO₂ of the gases inhaled ($PI_{co2}$) and exhaled by the patient under controlled conditions without rebreathing (ii) causing the patient to inhale a test gas containing at least a small concentration of CO₂ and continuing to measure the PCO₂ of the inspired and expired gases, the patient taking at least two breaths without rebreathing.

DETAILED DESCRIPTION OF THE DRAWINGS

Figure 1:
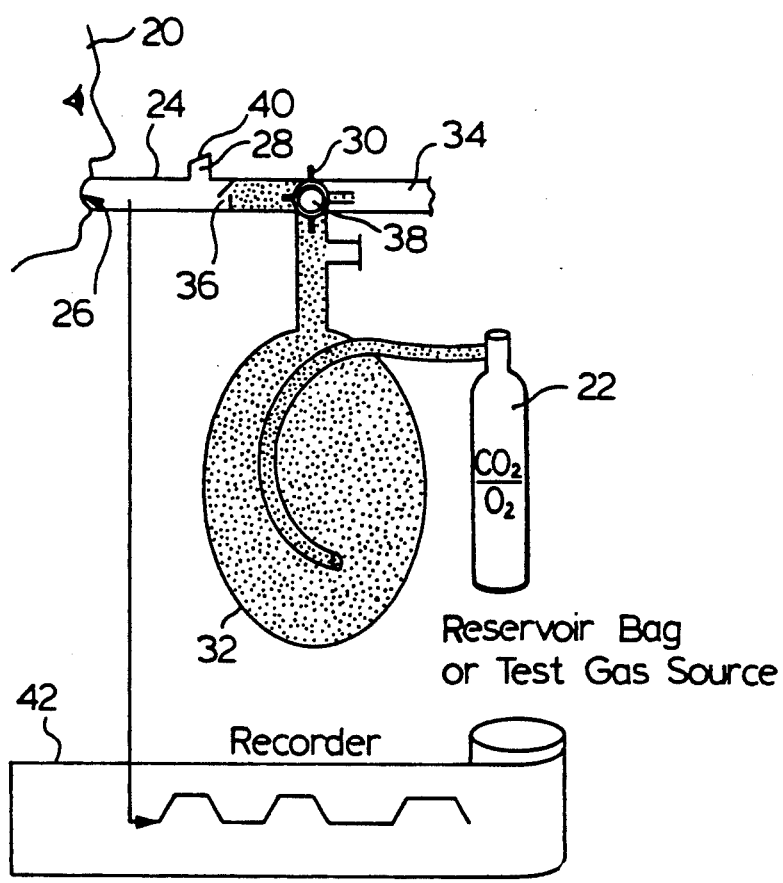
FIG. 1 is a schematic view of an apparatus used in a spontaneously breathing patient (without rebreathing), for determining the mixed venous PCO₂ (PvCO₂), during the beginning of inspiration.

With reference to FIG. 1 there is shown an apparatus for determining the mixed venous PCO₂ in a spontaneously breathing patient 20 without rebreathing during the beginning of inspiration of a test gas 22. Manifold 24 has a port 26 for communicating with the mouth of a patient 20; a port 28 for permitting exhaled gases to escape to the atmosphere; a port 30 for permitting entry of the test gas 22 from the reservoir 32 to the manifold 24; and, another port 34 to permit entry of room air therethrough for inhalation. With reference to manifold 24 there is provided a one-way valve 36 to permit both atmospheric gas and test gas 22 from the reservoir 32 to pass through the manifold 24 to the patient 20, but to preclude any gas exhaled by the patient 20 from passing through 17. Three-way valve 38 is positioned in the manifold 24 alternately allowing atmospheric gas or test gas 22 to pass through the manifold 24 to the patient 20. Another one-way valve 40 is positioned at exhaust port 28 to permit exhalation but preclude entry of atmospheric gas during inhalation; whereby upon inhalation either atmospheric or test gas 22 may be selected, using three-way valve 38, to pass through manifold 24 to the patient 20. A rapidly acting capnographic recorder 42 is provided for measuring the CO₂ concentration in the gas present in the manifold 24 proximate the mouth continuously during inhalation and expiration without rebreathing.

Figure 2:
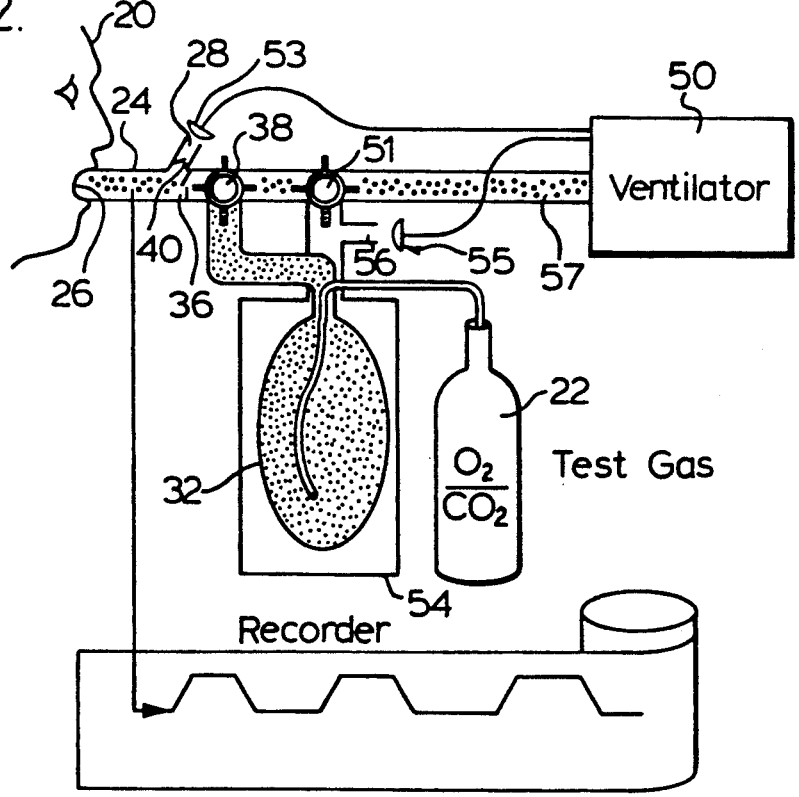
FIG. 2 is a schematic view of an apparatus used in a ventilated patient without rebreathing, for determining the mixed venous PCO₂ (PvCO₂), during the inspiration control phrase.

With reference to FIG. 2, there is shown an apparatus for determining the PvCO₂ in ventilated patients. The patient 20 is connected to a ventilator through a manifold 24 with attached three-way valve 51 open through to the ventilator. During the control inspiratory phase of the ventilator, gas 57 passes through the ventilator tubing 52, three-way valve 51 and three-way valve 38. Expiratory port 28 is closed by a mechanical valve 53 synchronous with the inspiratory phase of the ventilator. During the expiratory phase of the ventilator, one-way valve 36 prevents expired gas entering beyond it to prevent rebreathing. During the exhalation phase, mechanical valve 53 disengages and expired gas escapes past valve 40 through port 28 into the atmosphere.

Figure 3:
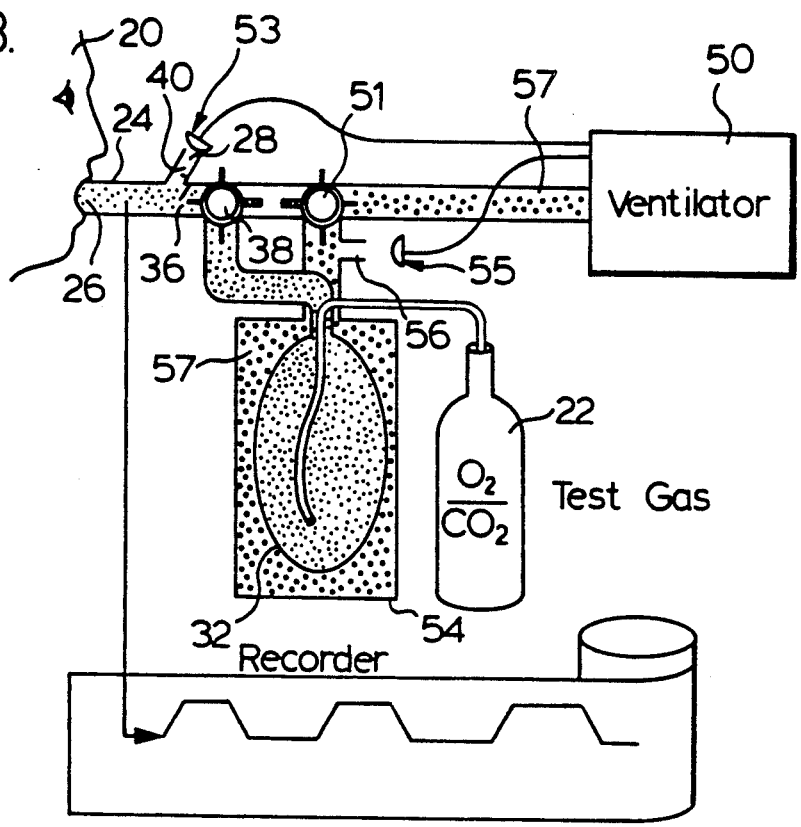
FIG. 3 is a schematic view of the apparatus in FIG. 2, during the inspiration test phase.

For effecting the test phase, in FIG. 3 is shown the same apparatus as in FIG. 2. During exhalation, the three-way valve 51 is turned to direct the ventilator flow into a rigid container 54 and valve 38 is turned to direct test gas from the reservoir 32 toward the manifold 24. During the inspiratory phase of the ventilator, a mechanical valve 55 occludes the opening 56 from the rigid container 54. Ventilator gas 57 enters the rigid container 54 and displaces an equal volume of test gas 22 from the reservoir and causes it to pass through valve 38, and one-way valve 36 to the patient. Port 28 is once again being closed off during inspiration by mechanical valve 53. At the end of the test phase, three-way valves 38 and 51 are once again returned to control configuration, once again allowing the ventilator gas 57 to enter the patient.

Alternatively the apparatus in FIGS. 2 and 3 can operate without valve 51. In the control phase during inhalation, the tidal volume put out by the ventilator would now be divided between that entering rigid container 54 (and compressing the gas therein) and that entering the patient. When the apparatus is used with a fixed volume ventilator, this would give a patient a tidal volume somewhat less than that put out by the ventilator. In the test phase, valve 38 is turned as before so that it blocks delivery of ventilator gas to the patient and diverts the whole ventilator gas volume into the rigid container 54. This will deliver an identical (and undiminished) tidal volume to the patient as apparatus system compliance is identical in the control and test phase.

With reference to the apparatus shown in FIGS. 1, 2, and 3, in using the apparatus to determine the mixed venous PCO₂ the following steps are taken. Capnographic recorder 42 is used to measure the PCO₂ of the atmospheric gases or ventilator gases 57, under control conditions. Patient 20 then inhales test gas 22 containing at least a small amount of CO₂, while the capnographic recorder continuously measures the PCO₂ of the test gas 22. Preferably the patient 20 takes three or four breaths of the test gas, but more than two breaths. The manifold valves 28, 36, 38 and/or 51 are then set to permit the patient 20 to return to breathing atmospheric gases or ventilator gases 57 under the same control conditions as previously. In this second control phase, the continuous monitoring of inspired gas ($P_I$) and the end tidal PCO₂ of expired gases does not stop. Thereafter, machine intelligence means may be used to calculate the relationships between the values measured by the capnographic recorder according to the mathematical relationships hereinafter described. Rationale:

When a person in a steady state breathes room air, at the end of exhalation, there is a constant concentration of $N_2$ in his lungs. If at the end of exhalation the person begins to inhale a gas free of $N_2$ (say 100% $O_2$), and one monitors continuously the exhaled concentrations of $N_2$ the end expiratory values will be described as a negative exponential approaching 0. This will be true assuming the amount of $N_2$ diffusing out of the blood is negligable compared to the amount washing out of the lungs. Assuming no dead space and instantaneous mixing, after a breath of size $V_T$, the expired $N_2$ concentration is:

$$FE = \frac{(FRC \times F_{FRC}) = (V_T \times F_I)}{V_T + FRC} \quad (1)$$

Where $F_E$ is the fractional concentration of gas in exhaled gas, FRC stands for the functional residual capacity which is the volume of gas left in the lung at the end of normal exhalation, $F_{FRC}$ is the fraction concentration of a gas in the FRC, $V_T$ is the tidal volume, or the volume of the breath, $F_I$ is the inspired fractional concentration of gas.

If one examines the difference between the inspired concentration and the expired concentration of $N_2$ after one breath of any test gas, subtracting $F_I$ from each side of equation (1) gives:

$$FE - F_I = \frac{(FRC \times F_{FRC}) + (V_T \times F_I)}{V_T + FRC} - F_I \quad (2)$$

Figure 4:
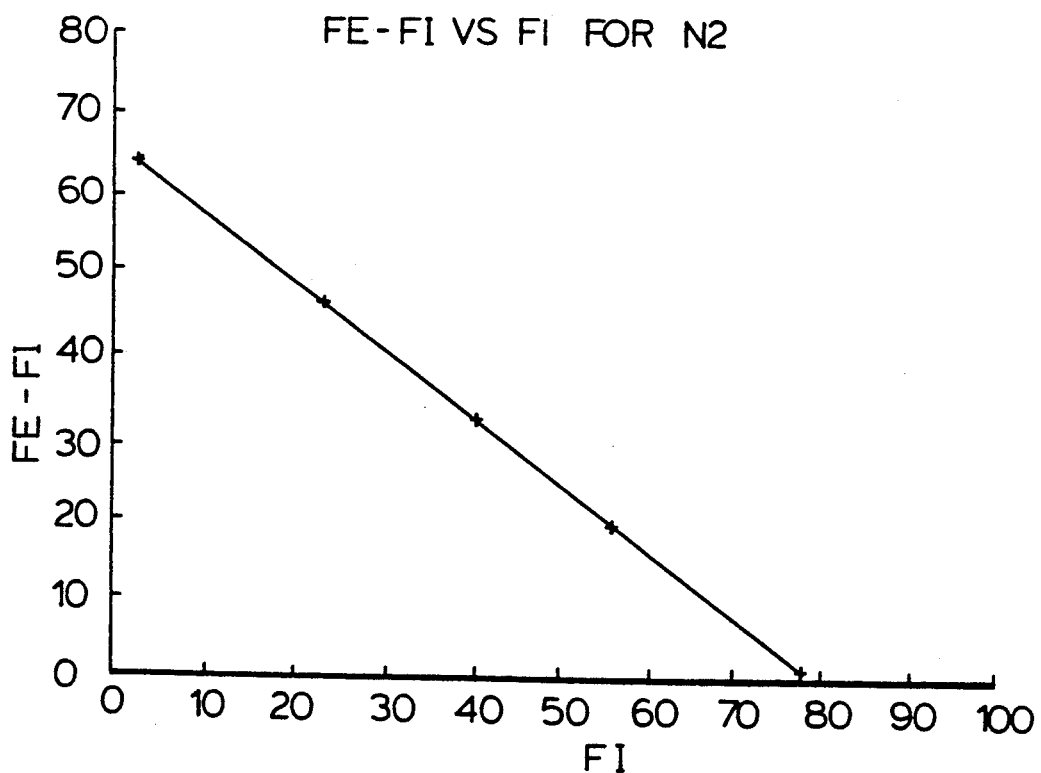
FIGS. 4 to 9 inclusive, are graphs of test

This can be rearranged to the form:

$$FE - F_I = \frac{V_T - 1}{V_T + FRC} \times F_I + \frac{FRC \times F_{FRC}}{V_T + FRC} \quad (3)$$

which is in the form of a linear relation $y = mx + b$. Indeed if one has a subject equilibrated with room air and he is given to inhale a breath of $N_2$ at various lower concentrations, one can then plot $FE - F_I$ vs. $F_I$ and get a straight line. The intercept of the x axis represents the original $F_{FRC}$. The slope is dependent on $V_T$ and FRC. This is illustrated in FIG. 4 using apparatus shown in FIG. 1.

Figure 5:
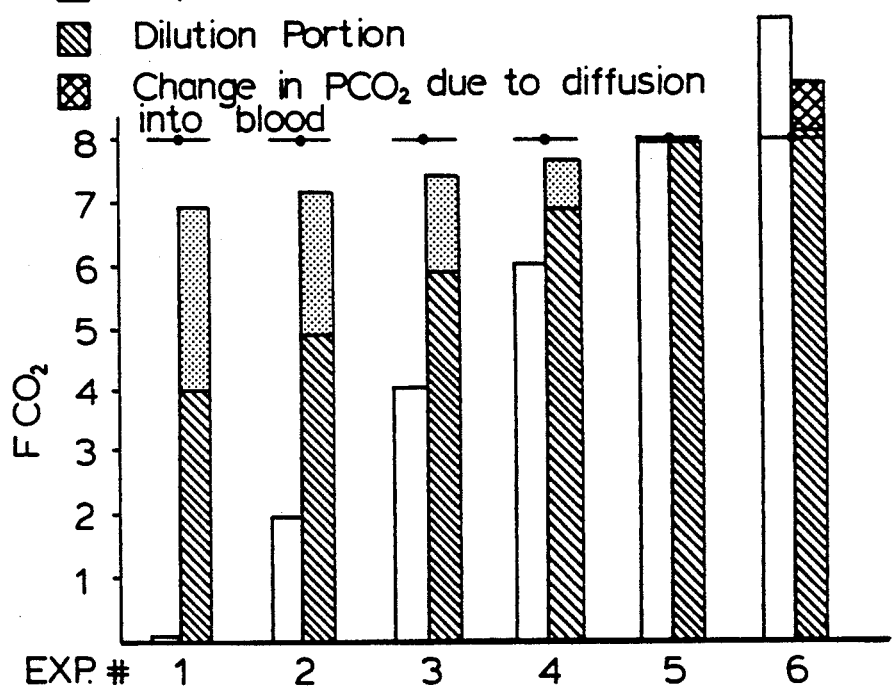
Figure 6:
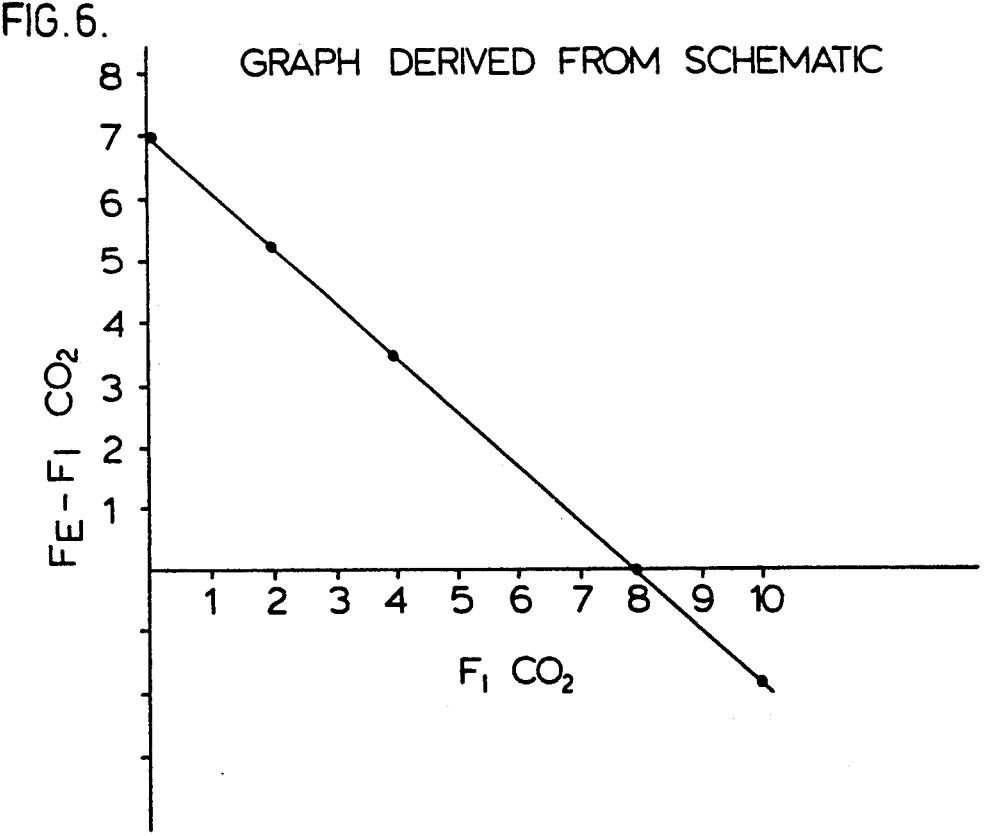

The relationships pertaining to $CO_2$ are somewhat more complex, carbon dioxide diffuses rapidly into the lung from the pulmonary capillaries after a breath of room air has diluted the lung concentration of $CO_2$. When viewed from the point of view of $F_E - F_I$, (To convert fractional concentration to partial pressure as used elsewhere in this application, the fractional concentration is multiplied by barometric pressure) the same linearity should hold in predicting the resultant $F_{FRC}$ at end inspiration. As has been pointed out by Knowles et al (Knowles H.H., Newman W., Fenn W.O., *Determination of Oxygenated, Mixed Venous Blood $CO_2$ Tension by a Breath-Holding Method.* J. Appl. Phpysiol 15(2) 225, 1960.) the amount of $CO_2$ diffusing into the lung should vary directly as the partial pressure gradient from the mixed venous blood to the lung. The words "vary directly as" imply a linear relationship. Thus the superimposition of these two linear relationships should yield a persistent linear relation. This rationale is illustrated in schematic form in FIGS. 5 and 6.

GENERAL OUTLINE OF METHOD AND DATA ANALYSIS

Generation of data

The subject breathes spontaneously or on a ventilator and is in a steady state with respect to gas exchange with the lung. After normal exhalation ventilation continues exactly the same only the inspired gas contains a new concentration of test gas, in this case $CO_2$. After three to five breaths, at end exhalation the circuit delivers again the original steady state gas. After a few minutes to allow a steady state to re-establish, the same procedure is repeated with a new inspired concentration of test gas. This can be repeated one or more times.

Calculation of $PvCO_2$

Inspired and expired $PCO_2$ is monitored constantly with a rapidly acting capnograph. Inspired concentrations of $CO_2$ are noted.

The end tidal $PCO_2$ of the third or fourth breath at each $FICO_2$ is noted. From breathing room air or $O_2$ in the control phase, the first point is obtained ($F_{I=}0$). A line is then generated that passes though any subsequent points of ($F_I$, $F_E - F_I$). This line is extrapolated to $F_E - F_{I=}0$. The place where it crosses the origin is taken as the $PvCO_2$.

Experimental Data

Figure 7:
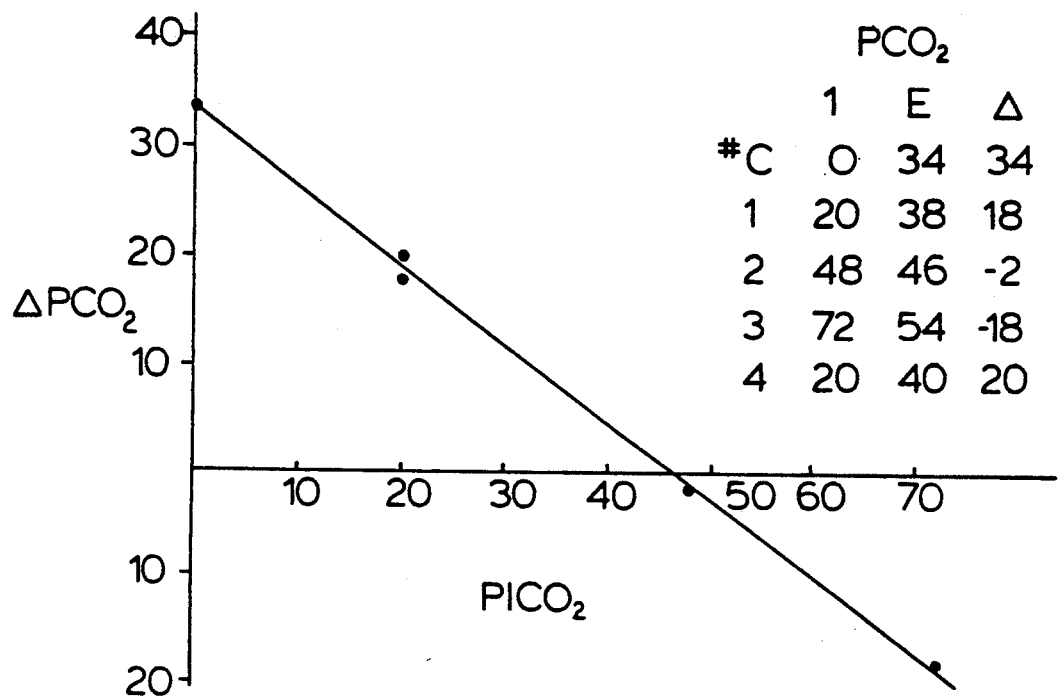

In one experiment a normal subject breathed three breaths of a gas containing a constant amount of $CO_2$, and then was returned to breathing room air. The experiment was repeated with four different inspired $CO_2$ concentrations. The results are graphed in FIG. 7.

Figure 8:
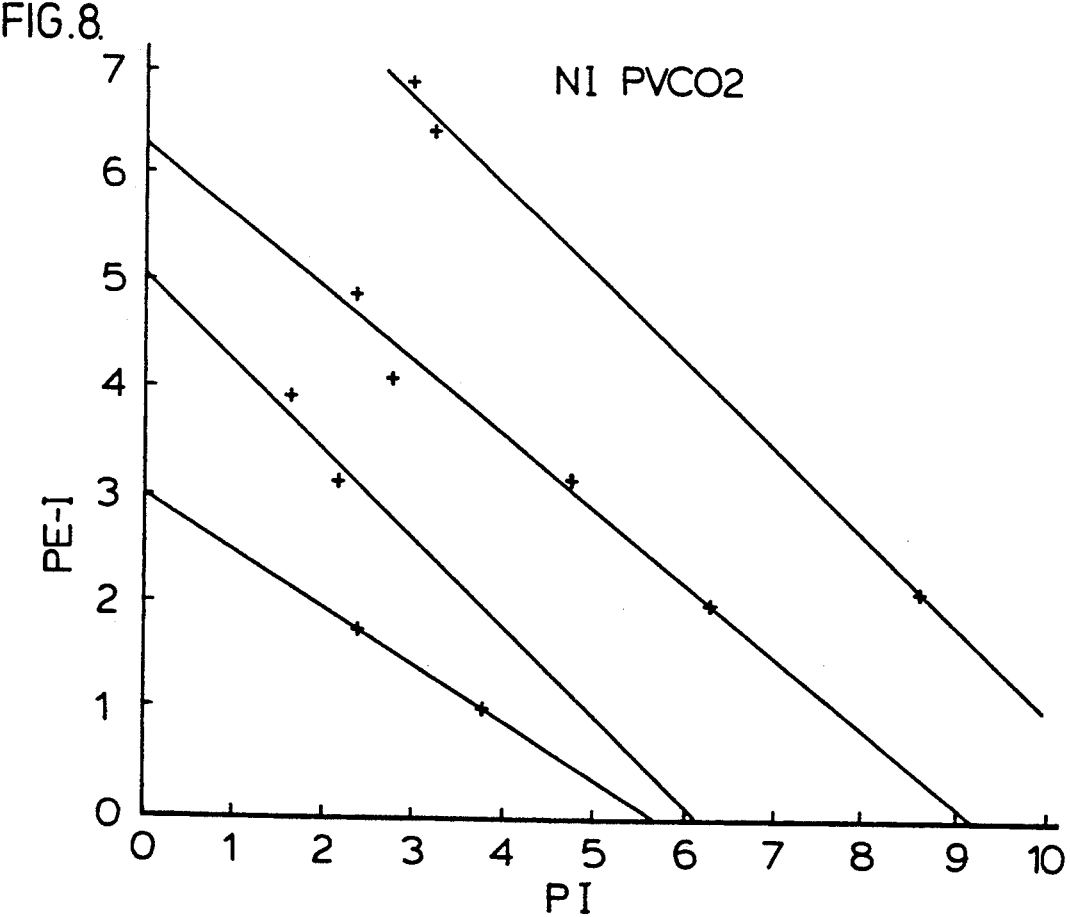
Figure 9:
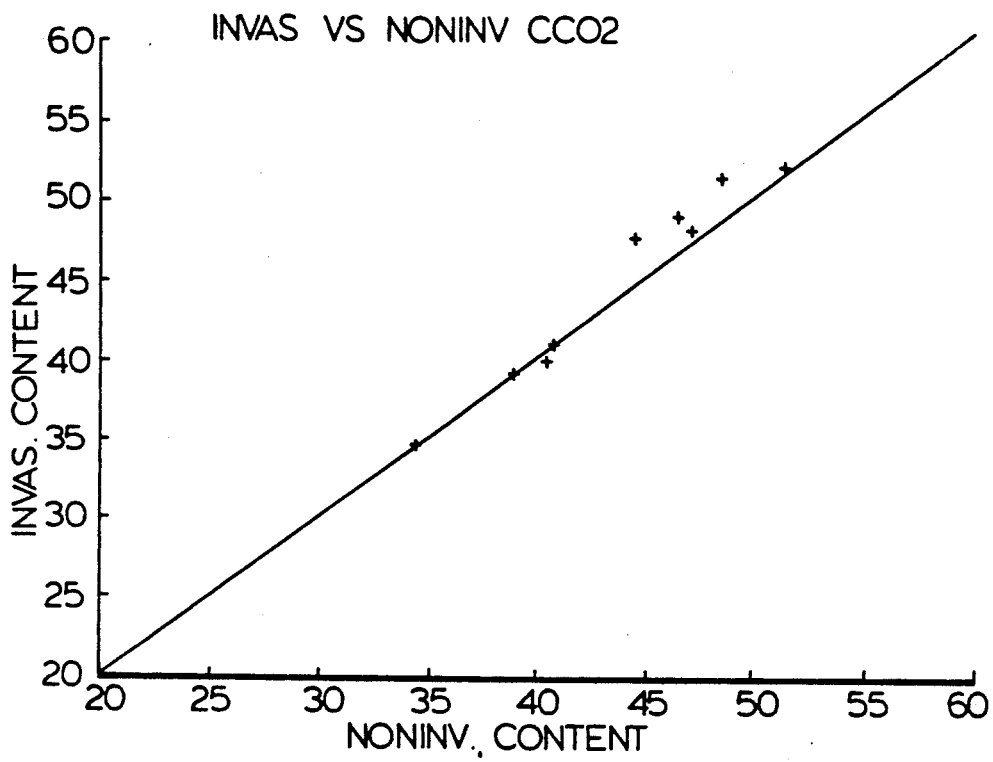

Mathematical analysis predicts that if one changes the $PvCO_2$ by changing the frequency of ventilation and keeping the $V_T$ constant, graphing $F_E - F_I$ vs. $F_I$ would yield a series of parallel lines. It also predicts that the x axis intercepts would predict the oxygenated $PvCO_2$. An experiment was set up in which paralyzed and ventilated dogs had catheters that allowed arterial and pulmonary arterial blood sampling. At a given minute ventilation, the dog was given various test gases containing a constant $PCO_2$ for three breaths. Between tests the dog was ventilated in a controlled manner. After a number of data points were obtained a new $PvCO_2$ was effected by changing the frequency of ventilation. FIG. 8 illustrates data points obtained in one dog with such a series of experiments. The correlation between the $CO_2$ content of the dog's blood as calculated from this noninvasive method as compared to the $CO_2$ content calculated from blood gas analysis of blood samples aspirated from the pulmonary artery is illustrated in FIG. 9.

These data show that the $PvCO_2$ predicted by the technique reflects exactly the true $PvCO_2$ to the limit of the accuracy of the $CO_2$ meters.

Figure 10:
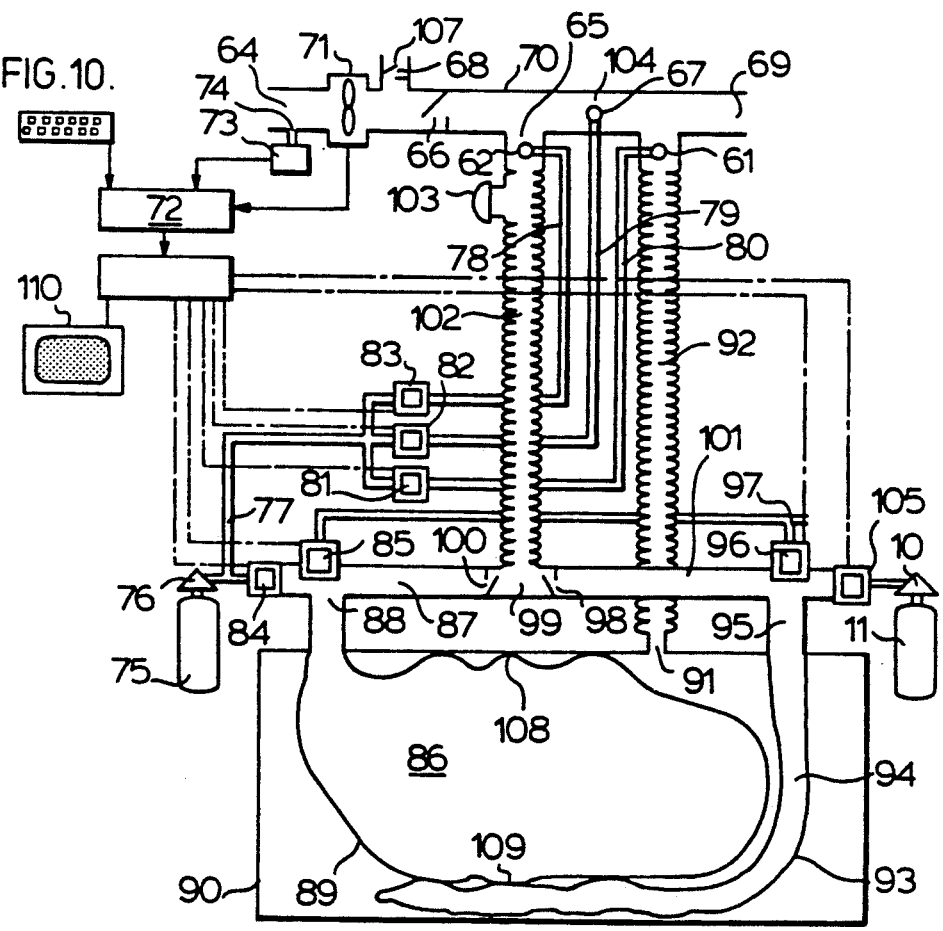
FIG. 10 is a schematic of another apparatus.

FIG. 10 is a schematic of an apparatus to carry out the method automatically in ventilated or spontaneously breathing patients according to an embodiment of the invention.

1. TESTING DURING SPONTANEOUS VENTILATION

In the control phase, the patient breathes through port 64. Ball valves 67 and 61 are collapsed and ball valve 62 is inflated occluding port 65. During inhalation, room air enters port 69 and passes along manifold 70 through one-way valve 66 (past one-way valve 68 which closes during inspiration) to the patient.

On passing the volume meter 71, the volume gas inspired is measured and input to the computer 72. Gas passing port 74 constantly sampled by the $CO_2$ and $N_2$ meter 73 and the concentration of $CO_2$ and $N_2$ is also input to the computer 72.

During exhalation, exhaled volume as measured by volume meter 71 and gas concentrations as measured by the $CO_2$ and $N_2$ meter is again input to the computer 72.

The computer then uses the input data to (a) compute minute ventilation, breath by breath and average it over a determined number of breaths; (b) determine the end tidal $PCO_2$; and (c) decide when a steady state is reached according to criteria previously decided upon.

During control breathing the machine prepares itself to deliver a test gas. Test gas 86 under high pressure in cylinder 75 is reduced to about 4PSI by regulator 76. This 4PSI is applied to circuit 77. Three-way solenoid valve 83 is open to ball valve 62 through tube 78, inflating the ball valve as previously mentioned. Three-way solenoid valves 82 and 81 open ball valves 67 and 61 respectively to room air, allowing them to be deflated. Two-way solenoid valve 84 is open to allow test gas 86 to enter manifold 87. Two-way solenoid 85 is closed to the manifold 87. Gas entering the manifold 87 enters through port 88 to fill reservoir 89. As the reservoir bag 89 fills, it displaces gas inside the rigid box 90. This gas passes from port 91 through hose 92 to atmosphere through port 69 or is part of the inhaled gas in port 64. The expanding reservoir 89 also compresses reservoir 93 squeezing out any residual test gas 94 through port 95 into manifold 101. Solenoid 105 closes off regulator 76 to manifold 101. As one-way valve 98 is closed by high pressure in manifold 99, and two-way solenoid 96 opens manifold 101 to atmosphere through port 97, test gas 94 escapes to atmosphere. When reservoir 89 is full and the pressure in the closed system which includes manifold 87 and 99 and hose 102 rises and reaches 50 cm $H_2O$, pressure pop-off valve 103 allows gas to escape, thus allowing test gas 86 to circulate from the cylinder 75, through the manifold 87, hose 102 and out the pop-off valve 103 thus washing out any other gases which may have contaminated this space and assuring a uniform concentration of test gas from reservoir 89 to ball valve 62.

When criteria that indicate the administration of a test gas are fulfilled, the computer 72 determines when the patient's next exhalation is occurring. During exhalation, solenoid valve 83 allows tube 78 to depressurize, and balloon valve 62 deflates. The gas 86, pressurizing hose 102, and reservoir 89 escapes through port 69 and some is puffed past valve 66 and 68 further reducing the "dead space" for the subsequent inspiration of test gas. Solenoids 84 and 85 close to the manifold 87. Solenoid 96 remains open to manifold 95. Solenoid 82 then allows balloon valve 67 to inflate occluding manifold at 104.

When the patient begins to inhale, valve 68 opens and the patient inhales test gas 86 from reservoir 89 through hose 102 and manifold 70. Exhalation is accomplished through port 107 as previously described. During exhalation the reservoir 89 is kept from collapsing by the fact that it is suspended from the box 90 at various points 108. Solenoid 84 may be opened for periods of time to provide some or all of the inspired gas during inspiration or refill reservoir 89 during exhalation.

After three or four breaths of test gas are taken by the subject, a change in solenoid 83 and 84 is effected to inflate balloon valve 62 and deflate balloon valve 67 and return the subject back to room air.

Throughout the test, volume and gas concentration data are recorded and stored in the computer.

If a second test gas application is desired, the following changes take place automatically: Solenoid 84 closes, solenoid 85 opens, solenoid 96 closes and solenoid 105 opens. This causes reservoir 93 to fill with gas 11, displace gas 86 from reservoir 89 and vent it through port 97. When reservoir 93 is full and manifold 101 is pressurized, valve 100 closes and the pressure in hose 102 rises until valve 103 pops off and flow of gas is effected from cylinder 11 out valve 103. This effectively washes out any previous test gas 86 that may have been present in hose 102.

When test gas is going to be administered, a corresponding series of changes in the valve are required for test gas 86.

To calculate the $PvCO_2$, the computer calculates a regression line through the series of points ($P_ICO_2$, $P_ECO_2$) and solves for the intercept of the x axis.

2. TESTING DURING MECHANICAL VENTILATION

When the subject is being ventilated by a machine such as a Bennet MA1 or MA2, Bear 1 or Bear 2 or Mohnehan ventilator, the manifold is interpassed between the endotracheal tube and the ventilator. Port 64 is attached to the endotracheal tube and the ventilator Y piece is attached to port 69. A mushroom valve is "T'd" to the ventilator's expiratory mushroom valve and applied to port 107 so that it occludes said port synchronous with occlusion of the ventilator's expiratory port.

(a) Control phase

Balloon valves 62 and 61 are inflated by solenoids 83 and 81. Balloon valve 67 is open to atmosphere and thus deflated. The inspiratory gas from the ventilator traverses manifold 70 and enters the patient. Port 107 is occluded by the ventilator's mushroom valve. During exhalation, valve 66 closes, the mushroom valve opens port 107 and exhaled gas escapes through it.

During control ventilation, gas 86 fills reservoir 89 in the same manner as during spontaneous ventilation.

To administer the test gas balloon valves 62 and 67 deflate and balloon valve 67 simultaneously inflates during exhalation. This time solenoid valve 96 remains open during the test phase. Solenoids 105 and 85 are closed. Solenoid 84 may be opened intermittently as required. Once again the gas pressurized in reservoir 86 flushes the space between port 65 and 107 with test gas 86.

During the inspiratory phase of the ventilator, the tidal volume is forced to enter box 90 by the inflated balloon valve 67. This displaces an equal volume of gas 86 from bag 89, which enters the patient through port 64. Exhalation takes place as described for control ventilations.

After three or four breaths of test gas, valves 61 and 62 reinflate, balloon valve 67 deflates and the patient inspires ventilator gas.

To apply a second test gas 94, reservoir 93 is inflated and reservoir 89 is vented by opening solenoid valves 105 and 85 and closing solenoid valves 84 and 96. When reservoir 93 is full and gas is venting through valve 103, solenoid 85 closes in anticipation of the next test phase.

The next test is applied in a manner directly corresponding to that described for gas 86.

The data is collected and analyzed as previously described.

Alternatively for controlled ventilation, a test may be applied in such a way to keep total apparatus compliance constant during inhalation of the control as well as the test phases. During inhalation of the control phase, if balloon valve 61 is deflated, solenoid valves 84, 85, 96 and 105 may be closed, effecting a closed system.

The cathode ray tube 110 may display information relevant to the workings of the machine as well as data in various stages of being processed.

Major components used to build the automated device are as follows:

| Component | Manufacturer | Catalog No. Identifying Feature |
|---|---|---|
| 1 way valve | Hans Rudolph Co. | 112261 |
| Pop off valve | Bird | 7862 |
| Solenoid valve assemblies 2-way and 3-way | Mac Valves Inc. | Manifold Assembly Part No. PTC-160-20 PTC-220-20 PTC-16-20 PTC-22-02 |
| Regulator | Medigas | |
| MCT Turbine Flow meter | K. L. Engineering | K-520 |
| Capnograph | Andros | Model 412 |
| Patient Manifold and Balloon Valve Assembly | Hans Rudolph Co. | 112260 | b) Rigid box was specially manufactured. Internal volume about 3 litres.

As many changes can be made to the embodiments without departing from the scope of the invention, it is intended that all matter contained herein shall be interpreted as illustrative of the invention and not in a limiting sense.

The embodiments of the invention in which an exclusive property or privilege is claimed are as follows:

1. An apparatus for use in determining the mixed venous $PCO_2$ ($PvCO_2$) comprising:
   (a) means permitting gases to be inhaled and exhaled by a patient;
   (b) means for measuring the $PCO_2$ of the gases inhaled and exhaled by the patient under controlled conditions without rebreathing
   (c) means for permitting the patient to inhale test gases containing at least a small concentration of $CO_2$ without rebreathing and means for measuring the $PCO_2$ of the inspired gases and the end tidal $PCO_2$ of the expired gases that result from breathing the test gases
   (d) a reservoir for the test gases to be inhaled, the test gases containing at least a small concentration of $CO_2$, the reservoir being in communication with the means permitting the gases to be inhaled.

2. The apparatus of claim 1, wherein the means for measuring the $PCO_2$ of the gases inhaled and exhaled by the patient under controlled conditions comprises a capnograph or mass spectrometer.

3. The apparatus as claimed in claim 2, wherein the means for permitting the patient to inhale the test gases containing at least a small concentration of $CO_2$ without rebreathing comprises:
   (i) a manifold having ports therein one port for communicating with the mouth of the patient, and another port for permitting entry of the test gas from the reservoir to the manifold
   (ii) two one-way valves, one such valve positioned in the manifold between an exhalation portion and the port leading to the reservoir to permit control gas and test gas to pass therethrough but preclude any exhaled gases from passing through it and the other such valve being positioned at the exhalation port permitting exhalation
   (iii) a three-way valve in the manifold for alternately allowing control gas or test gas to pass through the port for communicating with the mouth of the patient.

4. The apparatus of claim 3, wherein the means for permitting the patient to inhale the test gas containing at least a small concentration of $CO_2$ without rebreathing further comprises a second three-way valve positioned in the manifold on the side of the first three-way valve remote the port permitting exhalation of the expired gases, the second three-way valve for alternately permitting gases to pass from a ventilator to the port of the manifold though which ventilated gas may pass to the patient or be diverted to be used for pressurizing the reservoir containing a gas to be delivered to the patient whereby the first three-way valve is turned simultaneously with the second three-way valve in such a way as to permit the gases from either the ventilator or reservoir to pass through the part of the manifold leading to the patient's mouth to permit its use for patients being mechanically ventilated without rebreathing.

5. The apparatus of claim 1, wherein the apparatus further includes means for controlling the number of breaths of test gas taken and the means for measuring the $PCO_2$ of the gases inhaled and exhaled by the patient under controlled conditions without rebreathing comprises a capnograph or mass spectrometer.

6. The apparatus as claimed in claim 5, wherein the means permitting the patient to inhale the test gases containing at least small concentrations of $CO_2$ without rebreathing comprises:
   (i) a manifold having ports therein one port for communicating with the mouth of the patient, another port for permitting exhaled gases to escape to the atmosphere, another port for permitting entry of the test gas from the reservoir to the manifold and another port to permit entry of room air to the manifold for inhalation
   (ii) two one-way valves, one such valve positioned in the manifold between the exhalation portion and the port leading to the reservoir to permit control gas and test gases to pass therethrough but preclude any exhaled gases from passing through it and the other such valves being positioned at the exhalation port permitting exhalation but precluding entry of room air during inhalation
   (iii) a first three-way valve in the manifold for alternately allowing control condition gas or test gases to pass through the port for communicating with the mouth of the patent.

7. The apparatus of claim 6, wherein the means permitting the patient to inhale the test gases containing at least a small concentration of $CO_2$ without rebreathing further comprises a second three-way valve positioned in the manifold on the side of the first three-way valve remote the port permitting exhalation of the expired gases, the second three-way valve for alternately permitting gases to pass from a ventilator to the port of the manifold through which ventilated gas may pass to the patient or be diverted to be used for pressurizing the reservoir containing a gas to be delivered to the patient whereby the first three-way valve is turned simultaneously with the second three-way valve in such a way as to permit the gases from either the ventilator or reservoir to pass through the part of the manifold leading to the patient's mouth to permit its use for patients being mechanically ventilated without rebreathing.

8. The apparatus as claimed in claim 5, wherein the means permitting the patient to inhale the test gases containing at least a small concentration of $CO_2$ without rebreathing comprises:
   (i) a manifold having ports therein one port for communicating with the mouth of the patient, another port for permitting exhaled gases to escape to the atmosphere, another port for permitting entry of the test gas from the reservoir to the manifold and another port to permit entry of room air to the manifold for inhalation
   (ii) two one-way valves, one such valve positioned in the manifold between the exhalation portion and the port leading to the reservoir to permit control gas and test gases to pass therethrough but preclude any exhaled gases from passing through it and the other such valves being positioned at the exhalation port permitting exhalation but precluding entry of room air during inhalation
   (iii) a three-way valve in the manifold for alternately allowing control condition gas or test gas to pass through the port for communicating with the mouth of the patient.

9. The apparatus of claim 8, wherein the means permitting the patient to inhale the test gases containing at least a small concentration of $CO_2$ without rebreathing further comprises a second three-way valve positioned in the manifold on the side of the first three-way valve remote the port permitting exhalation of the expired gases, the second three-way valve for alternately permitting gases to pass from a ventilator to the port of the manifold through which ventilated gas may pass to the patient to be diverted to be used for pressurizing the reservoir containing a gas to delivered to the patient whereby the first three-way valve is turned simultaneously with the second three-way valve in such a way as to permit the gases from either the ventilator or reservoir to pass through the part of the manifold leading to the patient's mouth to permit its use for patients being mechanically ventilated without rebreathing.

10. The apparatus of claim 1, further comprising means to determine the difference between the end tidal $PCO_2$ and inspired $PCO_2$ under control and test conditions and means for relating said difference of the inspired $PCO_2$ used in the determination of said difference to mathematically determine the $PvCO_2$ wherein the means for measuring the $PCO_2$ of the gases inhaled and exhaled by the patient under controlled conditions comprises a capnograph or mass spectrometer.

11. The apparatus as claimed in claim 10, wherein the means permitting the patient to inhale the test gases containing at least small concentrations of $CO_2$ without rebreathing comprises:
   (i) a manifold having ports therein one port for communicating with the mouth of the patient, another port for permitting exhaled gases to escape to the atmosphere, another port for permitting entry of the test gas from the reservoir to the manifold and another port to permit entry of room air to the manifold for inhalation
   (ii) two one-way valves, one such valve positioned in the manifold between the exhalation portion and the port leading to the reservoir to permit control gas and test gases to pass therethrough but preclude any exhaled gases from passing through it and the other such valves being positioned at the exhalation port permitting exhalation but precluding entry of room air during inhalation
   (iii) a first three-way valve in the manifold for alternately allowing control condition gas or test gases to pass through the port for communicating with the mouth of the patent.

12. The apparatus of claim 11, wherein the means permitting the patient to inhale the test gases containing at least a small concentration of $CO_2$ without rebreathing further comprises a second three-way valve positioned in the manifold on the side of the first three-way valve remote the port permitting exhalation of the expired gases, the second three-way valve for alternately permitting gases to pass from a ventilator to the port of the manifold through which ventilated gas may pass to the patient or be diverted to be used for pressurizing the reservoir containing a gas to be delivered to the patient whereby the first three-way valve is turned simultaneously with the second three-way valve in such a way as to permit the gases from either the ventilator or reservoir to pass through the part of the manifold leading to the patient's mouth to permit its use for patients being mechanically ventilated without rebreathing.

13. The apparatus of claim 12, wherein the means to determine the difference between the end tidal $PCO_2$ and inspired $PCO_2$ under control and test conditions and means for relating said difference to the inspired $PCO_2$ used in the determination of said difference comprises a computer and requisite computer programming means for determining mixed venous $PCO_2$.

14. The apparatus of claim 11, wherein the means to determine the difference between the end tidal $PCO_2$ and inspired $PCO_2$ under control and test conditions and means for relating said difference to the inspired $PCO_2$ used in the determination of said difference comprises a computer and requisite computer programming means for determining mixed venous $PCO_2$.

15. The apparatus as claimed in claim 10, wherein the means permitting the patient to inhale the test gases containing at least a small concentration of $CO_2$ without rebreathing comprises:
   (i) a manifold having ports therein one port for communicating with the mouth of the patient, another port for permitting exhaled gases to escape to the atmosphere, another port for permitting entry of the test gas from the reservoir to the manifold and another port to permit entry of room air to the manifold for inhalation
   (ii) two one-way valves, one such valve positioned in the manifold between the exhalation portion and the port leading to the reservoir to permit control gas and test gases to pass therethrough but preclude any exhaled gases from passing through it and the other such valves being positioned at the exhalation port permitting exhalation but precluding entry of room air during inhalation
   (iii) a three-way valve in the manifold for alternately allowing control condition gas or test gas to pass through the port for communicating with the mouth of the patient.

16. The apparatus of claim 15, wherein the means permitting the patient to inhale the test gases containing at least a small concentration of $CO_2$ without rebreathing further comprises a second three-way valve positioned in the manifold on the side of the first three-way valve remote the port permitting exhalation of the expired gases, the three-way valve for alternately permitting gases to pass from a ventilator to the port of the manifold through which ventilated gas may pass to the patient or be diverted to be used for pressurizing the reservoir containing a gas to be delivered to the patient whereby the first three-way valve is turned simultaneously with the second three-way valve in such a way as to permit the gases from either the ventilator or reservoir to pass through the part of the manifold leading to the patient's mouth to permit its use for patients being mechanically ventilated without rebreathing.

17. The apparatus of claim 16, wherein the means to determine the difference between the end tidal $PCO_2$ and inspired $PCO_2$ under control and test conditions and means for relating said difference to the inspired $PCO_2$ used in the determination of said difference comprises a computer and requisite computer programming means for determining mixed venous $PCO_2$.

18. The apparatus of claim 15, wherein the means to determine the difference between the end tidal $PCO_2$ and inspired $PCO_2$ under control and test condition and means for relating said difference to the inspired $PCO_2$ used in the determination of said difference comprises a computer and requisite computer programming means for determining mixed venous $PCO_2$.

19. The apparatus of claim 10, wherein the means to determine the difference between the end tidal $PCO_2$ and inspired $PCO_2$ under control and test conditions and means for relating said difference to the inspired $PCO_2$ used in the determination of said difference comprises a computer and requisite computer programming means for determining mixed venous $PCO_2$.

20. The apparatus as claimed in claim 1, wherein the means for permitting the patient to inhale the test gases containing at least a small concentration of $CO_2$ without rebreathing comprises:
  (i) a manifold having ports therein one port for communicating with the mouth of the patient, and another port for permitting entry of the test gas from the reservoir to the manifold
  (ii) two one-way valves, one such valve positioned in the manifold between an exhalation portion and the port leading to the reservoir to permit control gas and test gases to pass therethrough but preclude any exhaled gases from passing through it and the other such valve being positioned at the exhalation port permitting exhalation
  (iii) a first three-way valve in the manifold for alternately allowing the control gas or test gases to pass through the port for communicating with the mouth of the patient.

21. The apparatus of claim 20, wherein the means for permitting the patient to inhale the test gases containing at least a small concentration of $CO_2$ without rebreathing further comprises a second three-way valve positioned in the manifold on the side of the first three-way valve remote the port permitting exhalation of the expired gases, the second three-way valve for alternately permitting gases to pass from a ventilator to the port of the manifold through which ventilated gas may pass to the patient or be diverted to be used for pressurizing the reservoir containing a gas to be delivered to the patient whereby the first three-way valve is turned simultaneously with the second three-way valve in such a way as to permit the gases from either the ventilator or reservoir to pass through the port of the manifold leading to the patient's mouth to permit its use for patients being mechanically ventilated without rebreathing.

22. The apparatus of claim 1, wherein the apparatus further includes means for controlling the number of breaths of test gas taken.

23. The apparatus of claim 22, further comprising means to determine the difference between the end tidal $PCO_2$ and inspired $PCO_2$ under control and test conditions and means for relating said difference to the inspired $PCO_2$ used in the determination of said difference to mathematically determine the $PvCO_2$.

24. The apparatus of claim 1, further comprising means to determine the difference between the end tidal $PCO_2$ and inspired $PCO_2$ under control and test conditions and means for relating said difference to the inspired $PCO_2$ used in the determination of said difference to mathematically determine the $PvCO_2$.

25. An apparatus for determining cardiac output using the procedure described by Gideon in A New Method For Non-Invasive Determination of Pulmonary Blood Flow, Med. & Biol. Eng. and Compute., Volume 18, P. 411 (1980) which discloses the ventilating of a patient in steady state, said apparatus comprising:
  (a) means permitting gases to be inhaled and exhaled by a patient;
  (b) means for measuring the $PCO_2$ of the gases inhaled and exhaled by the patient under controlled conditions without rebreathing (c) means for permitting the patient to inhale test gases containing at least a small concentration of $CO_2$ without rebreathing and means for measuring the $PCO_2$ of the inspired gases and the end tidal $PCO_2$ of the expired gases that result from breathing the test gases
  (d) a reservoir for the test gases to be inhaled, the test gases containing at least a small concentration of $CO_2$, the reservoir being in communication with the means permitting the gases to be inhaled wherein the means for measuring the $PCO_2$ of the gases inhaled and exhaled by the patient under controlled conditions comprises a capnograph or mass spectrometer and further comprising means for calculating breath by breath, minute $CO_2$ production for different test gases without rebreathing.

* * * * *